United States Patent [19]

Fellous et al.

[11] Patent Number: 5,171,867
[45] Date of Patent: Dec. 15, 1992

[54] METHOD OF PREPARING 2,5-DIMETHYL-4-HYDROXY-2H-FURAN-3-ONE

[75] Inventors: Roland Fellous, Cagnes/S/Mer; Gérard George, Nice, both of France

[73] Assignee: Sanofi, Paris, France

[21] Appl. No.: 727,624

[22] Filed: Jul. 10, 1991

[30] Foreign Application Priority Data

Jul. 10, 1990 [FR] France .................. 90 08772

[51] Int. Cl.$^5$ .............................. C07D 307/32
[52] U.S. Cl. ...................... 549/477; 549/479
[58] Field of Search ..................... 549/477, 479

[56] References Cited

U.S. PATENT DOCUMENTS

| | | | |
|---|---|---|---|
| 3,629,292 | 12/1971 | Evers | 260/347.8 |
| 4,181,666 | 1/1980 | Huber et al. | 260/347.8 |
| 4,208,338 | 6/1980 | Huber et al. | 260/347.8 |
| 4,294,767 | 10/1981 | Eschinasi et al. | 549/477 |
| 4,464,409 | 8/1984 | de Rooij | 549/477 |

OTHER PUBLICATIONS

Helv. Chim. Acta, 46, 1259 (1963).
Helv. Chim. Acta, 49, 53–56 (1966).
Chemistry Letters, pp. 495–498 (1976).
Chemical Abstract, vol. 72 (1970) entry 31598s abstracting Swiss patent 474,500.
Chemical Abstract, vol. 72 (1970) entry 66795f abstracting Swiss patent 474,501.
Synthesis, p. 754, (1977).

Primary Examiner—C. Warren Ivy
Assistant Examiner—Ba K. Trinh
Attorney, Agent, or Firm—Foley & Lardner

[57] ABSTRACT

The present invention relates to a method of preparing 2,5-dimethyl-4-hydroxy-2H-furan-3-one. It consists in reacting hydrogen peroxide with 2,5-dimethyl-2H-furan-3-one in the presence of a base.

16 Claims, No Drawings

METHOD OF PREPARING 2,5-DIMETHYL-4-HYDROXY-2H-FURAN-3-ONE

The present invention relates to a novel method of preparing 2,5-dimethyl-4-hydroxy-2H-furan-3-one, a compound which smells of caramel and is used in the food industry and the perfume industry.

Various methods of preparing this product have been proposed; thus Helv. Chim. Acta, 49, p. 53–56 (1966) describes its preparation from hexan-4-ol-2,3,5-trione.

Swiss patents 474 500 and 474 501 describe its preparation by cyclization of the hexanedioldiones $CH_3COCHOHCHOHCOCH_3$ and $CH_3CHOHCOCOCHOHCH_3$, and German patents 2 105 014 and 2 831 673 describe its preparation by cyclization of the derivatives of the formula $CH_3CHXCOCOCHXCH_3$, in which X is Cl or Br. Its preparation by oxidation of the dihydrofuranones of formula A:

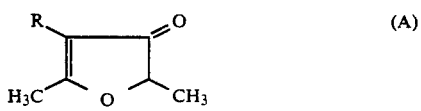

has also been proposed in Canadian patent 1 132 591 and German patent 2 359 891, R being CN and COOH respectively.

The method according to the invention also involves the oxidation of a dihydrofuranone, but the method of preparing the latter is simpler than the preparation of the compounds of formula A.

In fact, the method of the invention consists in reacting hydrogen peroxide with 2,5-dimethyl-2H-furan-3-one of formula I:

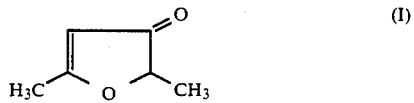

in the presence of a base.

The reaction is advantageously carried out in homogeneous phase at a temperature of about between 20° C. and 80° C. Solvents which can be used are a mixture of water and of an alcohol, such as methanol or ethanol, or a mixture of water and of a ketone such as acetone. Alkali metal hydroxides and carbonates may be mentioned among the bases which may be used.

2,5-Dimethyl-2H-furan-3-one is a known product which may be prepared for example from diacetyl, $H_3CCOCOCH_3$, by the method described in Synthesis, p. 754 (1977), or by reacting a 2-bromopentanoyl halide with the sodium salt of 3-oxobutanoic acid by the method described in French patent A-2 211 457, or else from a 2,5-dimethylfuran-3-carboxylic acid ester as mentioned in Helv. Chim. Acta, 46, 1259 (1963).

Examples of how to carry out the invention are described below.

EXAMPLE 1

378 g of 2,5-dimethyl-2H-furan-3-one are added to a solution of 304 g of potassium bicarbonate in 420 ml of methanol and 420 ml of water, and 372 ml of 30% (w/w) hydrogen peroxide are then added over 1 hour, under stirring, the temperature being kept between 30° and 40° C.

After stirring for 2 hours at about 20° C., the starting material and the desired product are extracted from the reaction medium in 500 ml of ethyl acetate using a liquid-liquid extraction apparatus.

The solvent is removed under vacuum to give 160 g of a brownish oil, which is distilled under reduced pressure. The fraction distilling at about 100° C. under 250 Pa is isolated and crystallized from twice its weight of ethyl acetate or isopropyl ether.

This gives 25 g of 2,5-dimethyl-4-hydroxy-2H-furan-3-one.

40 g of starting material are recovered from the fraction distilling below 100° C. and may be recycled.

EXAMPLE 2

56 g of 2,5-dimethyl-2H-furan-3-one are dissolved in 390 ml of methanol and this solution is mixed with 110 ml of 30% (w/w) hydrogen peroxide. An aqueous solution of sodium hydroxide (9.4 g of NaOH pellets in 33 g of water) is added to this medium, under stirring. After stirring for 4 hours 30 minutes at 60° C., the yield of the final product is 12%.

EXAMPLE 3

The procedure of Example 2 is followed except that ethanol is used instead of methanol as solvent; the yield is then 4%.

EXAMPLE 4

56 g of 2,5-dimethyl-2H-furan-3-one are added to a mixture of 390 ml of methanol and 140 g of a saturated solution of sodium carbonate, and 111 ml of 30% (w/w) hydrogen peroxide are then added over 1 hour; after 4 hours at 70° C., the yield of the expected product is found by gas chromatography to be 11%.

What is claimed is:

1. A method of preparing 2,5-dimethyl-4-hydroxy-2H-furan-3-one, which comprises the step of reacting 2,5-dimethyl-2H-furan-3-one with hydrogen peroxide in a mixture of an alcohol and water as solvent and in the presence of a base.

2. A method according to claim 1, wherein said base is an alkali metal hydroxide or carbonate.

3. A method according to claim 2, wherein said base is sodium hydroxide and wherein the reaction is carried out in a homogeneous phase in a mixture of methanol and water.

4. A method according to claim 1, wherein said alcohol is methanol or ethanol.

5. A method according to claim 2, wherein said base is potassium bicarbonate or sodium carbonate.

6. A method according to claim 1, wherein said reaction is carried out in a homogeneous phase at a temperature of between about 20° C. and 80° C.

7. A method according to claim 7, wherein said alcohol is methanol or ethanol.

8. A method according to claim 1, wherein said base is potassium bicarbonate and said alcohol is methanol.

9. A method according to claim 1, wherein said base is potassium bicarbonate and said alcohol is ethanol.

10. A method according to claim 1, wherein said base is sodium carbonate and said alcohol is methanol.

11. A method according to claim 1, wherein said base is an alkali metal carbonate and said alcohol is methanol or ethanol.

12. A method according to claim ,1 wherein said base is an alkali metal hydroxide and said alcohol is methanol or ethanol.

13. A method according to claim 11, wherein said reaction is carried out in a homogeneous phase at a temperature of between about 20° C. and 80° C.

14. A method according to claim 12, wherein said reaction is carried out in a homogeneous phase at a temperature of between about 20°0 C. and 80° C.

15. A method according to claim 12, wherein said base is sodium hydroxide.

16. A method according to claim 1, which further comprises the step of isolating 2,5-dimethyl-4-hydroxy-2H-furan-3-one from said solvent.

* * * * *